(12) United States Patent
Boyd et al.

(10) Patent No.: US 9,662,449 B2
(45) Date of Patent: *May 30, 2017

(54) NEEDLE-FREE INJECTORS AND DESIGN PARAMETERS THEREOF THAT OPTIMIZE INJECTION PERFORMANCE

(71) Applicant: ZOGENIX, INC., Emeryville, CA (US)

(72) Inventors: Brooks M. Boyd, Berkeley, CA (US); Jeffrey A. Schuster, Bolinas, CA (US)

(73) Assignee: Zogenix, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,977

(22) Filed: Jan. 15, 2016

(65) Prior Publication Data
US 2016/0129191 A1 May 12, 2016

Related U.S. Application Data

(63) Continuation of application No. 14/251,959, filed on Apr. 14, 2014, now Pat. No. 9,265,888, which is a continuation of application No. 13/232,820, filed on Sep. 14, 2011, now Pat. No. 8,734,384.

(60) Provisional application No. 61/383,205, filed on Sep. 15, 2010.

(51) Int. Cl.
*A61M 5/30* (2006.01)
*A61K 31/404* (2006.01)
*A61K 39/395* (2006.01)

(52) U.S. Cl.
CPC ......... *A61M 5/3007* (2013.01); *A61K 31/404* (2013.01); *A61K 39/395* (2013.01); *A61M 5/30* (2013.01)

(58) Field of Classification Search
CPC .............................. A61M 5/30; A61M 5/3007
USPC ........................................................... 604/68
See application file for complete search history.

(56) References Cited

U.S. PATENT DOCUMENTS

| 3,859,996 A | 1/1975 | Mizzy et al. |
| 5,399,163 A | 3/1995 | Peterson et al. |
| 5,480,381 A | 1/1996 | Weston |
| 5,891,086 A | 4/1999 | Weston |

(Continued)

FOREIGN PATENT DOCUMENTS

| EP | 0 063 341 | 10/1982 |
| EP | 0 063 342 | 10/1982 |

(Continued)

*Primary Examiner* — Kevin C Sirmons
*Assistant Examiner* — Deanna K Hall
(74) *Attorney, Agent, or Firm* — Karl Bozicevic; Bozicevic, Field & Francis LLP

(57) ABSTRACT

A needle free injector system and a method for delivering a formulation using this system are disclosed. The method comprises actuating a needle free injector to pressurize a liquid formulation and force the formulation through an orifice in a skin puncture phase followed by injection of the formulation during a delivery phase. The skin puncture phase is defined by a pressure profile vs. time curve after actuation which has a main pressure peak with a maximum pressure. The delivery phase occurs at a lower pressure than the maximum pressure of the main peak pressure. The device may have one or more orifices and pressurizing the formulation during the puncture phase and delivery phase to extrude the formulation through each orifice is structured so as to improve characteristics of needle free delivery.

14 Claims, 10 Drawing Sheets

(56) References Cited

U.S. PATENT DOCUMENTS

| | | |
|---|---|---|
| 5,957,886 A | 9/1999 | Weston |
| 6,135,979 A | 10/2000 | Weston |
| 6,149,625 A | 11/2000 | Weston et al. |
| 6,174,304 B1 | 1/2001 | Weston |
| 6,179,583 B1 | 1/2001 | Weston |
| 6,216,493 B1 | 4/2001 | Weston et al. |
| 6,251,091 B1 | 6/2001 | Weston |
| 6,258,059 B1 | 7/2001 | Weston et al. |
| 6,280,410 B1 | 8/2001 | Weston et al. |
| 6,409,032 B1 | 6/2002 | Bekkers et al. |
| 6,415,631 B1 | 7/2002 | Weston et al. |
| 6,554,818 B2 | 4/2003 | Weston et al. |
| 6,620,135 B1 | 9/2003 | Weston et al. |
| 8,591,457 B2 | 11/2013 | Gilbert |
| 8,734,384 B2 * | 5/2014 | Boyd ............... A61M 5/30 604/140 |
| 9,265,888 B2 * | 2/2016 | Boyd ............... A61M 5/30 |
| 2002/0087117 A1 | 7/2002 | Stout et al. |
| 2004/0133150 A1 | 7/2004 | Hjertman et al. |
| 2005/0154347 A1 | 7/2005 | Neracher |
| 2008/0119783 A1 * | 5/2008 | Green ............... A61M 5/30 604/68 |

FOREIGN PATENT DOCUMENTS

| | | |
|---|---|---|
| EP | 0 133 471 | 2/1985 |
| EP | 0 347 190 | 12/1989 |
| EP | 0 427 457 | 5/1991 |
| JP | 2003507134 | 2/2003 |
| JP | 2007-44529 | 2/2007 |
| JP | 2008-284375 | 11/2008 |
| JP | 2010155060 | 7/2010 |
| WO | 82/02835 | 9/1982 |
| WO | 89/08469 | 9/1989 |
| WO | 92/08508 | 5/1992 |
| WO | 93/03779 | 3/1993 |
| WO | 94/02188 A1 | 2/1994 |
| WO | 95/03844 | 2/1995 |
| WO | 02051470 | 7/2002 |
| WO | 2006009839 | 1/2006 |
| WO | 2006/086774 A2 | 8/2006 |
| WO | WO 2007/083518 | 7/2007 |
| WO | 2008/027579 A1 | 3/2008 |

* cited by examiner

| Configuration Number | Trial Number | Trial Name | Orifice (mm) | Converted Gas Chamber Pressure (mg) | Number of Injections (in-vivo) | Number of Actuations (in-vitro) |
|---|---|---|---|---|---|---|
| 13 | 12-0083C | B1 | 0.350 | 115 | 100 | 5 |
| 14 | 12-0083D | B1 | 0.330 | 115 | 100 | 5 |
| 313 & 15 | 12-0084AB | B2 | 0.381 | 136 | 198 | 50 |
| 16 & 17 | 12-0084CD | B2 | 0.381 | 115 | 200 | 50 |
| 196 | P095 | C | 0.295 | 127 | 101 | 25 |
| 198 | P095 | C | 0.295 | 141 | 100 | 25 |
| 199 | P095 | C | 0.295 | 162 | 100 | 24 |
| 200 | P095 | C | 0.340 | 127 | 149 | 25 |
| 202 | P095 | C | 0.340 | 134 | 149 | 25 |
| 204 | P095 | C | 0.340 | 141 | 150 | 25 |
| 206 | P095 | C | 0.340 | 150 | 150 | 25 |
| 208 | P095 | C | 0.340 | 162 | 100 | 25 |
| 209 | P095 | C | 0.385 | 127 | 202 | 25 |
| 211 | P095 | C | 0.385 | 134 | 202 | 25 |
| 213 | P095 | C | 0.385 | 141 | 199 | 24 |
| 215 | P095 | C | 0.385 | 150 | 200 | 25 |
| 217 | P095 | C | 0.385 | 162 | 100 | 24 |
| 218 | P095 | C | 0.435 | 127 | 100 | 25 |
| 219 | P095 | C | 0.435 | 134 | 99 | 25 |
| 220 | P095 | C | 0.435 | 141 | 101 | 25 |
| 221 | P095 | C | 0.435 | 150 | 101 | 25 |
| 222 | P095 | C | 0.435 | 162 | 102 | 25 |
| 400 | CPV | CPV | 0.410 | 165 | 1152 | 25 |
| Total | | | - | - | 4155 | 582 |

FIG. 6

| Sorce | Sum of Squares | DF | Mean Square | F Value | Prob > F |
|---|---|---|---|---|---|
| Model | 0.73 | 4 | 0.18 | 46.69 | <0.0001 |
| Orifice Size | 0.018 | 1 | 0.018 | 4.59 | 0.0533 |
| Gas Mass | 0.67 | 1 | 0.67 | 172.63 | <0.0001 |
| Orifice Size$^2$ | 0.023 | 1 | 0.023 | 5.79 | 0.0332 |
| Gas Mass$^2$ | 0.029 | 1 | 0.029 | 7.53 | 0.0178 |
| Residual | 0.047 | 12 | 3.896E-003 | | |
| Cor Total | 0.77 | 16 | | | |

| | | | |
|---|---|---|---|
| Std. Dev. | 0.062 | R-Squared | 0.9396 |
| Mean | 3.64 | Adj R-Squared | 0.9195 |
| C.V. | 1.72 | Pred R-Squared | 0.8816 |
| PRESS | 0.092 | Adeq Precision | 20.160 |

FIG. 9

| Trial Number | Orifice (mm) | Gas Mass (mg) | Actual VAS | Predicted VAS | 95% Prediction Interval | | Prediction Error | |
|---|---|---|---|---|---|---|---|---|
| | | | | | Lower PI | Upper PI | Min | Max |
| 12-0077A | 0.300 | 136 | 3.75 | 3.80 | 3.64 | 3.96 | -2.4% | +3.2% |
| P095 | 0.435 | 150 | 3.42 | 3.47 | 3.31 | 3.63 | | |

FIG. 10

NEEDLE-FREE INJECTORS AND DESIGN PARAMETERS THEREOF THAT OPTIMIZE INJECTION PERFORMANCE

FIELD OF THE INVENTION

The present invention relates to delivery of liquid drug formulations utilizing needle-free injection, and specifically relates to parameters related to the formulation pressure profile during delivery that can be used to optimize injection performance using needle-free injection technology. The proper choice of these parameters can be used to optimize the desired level of successful injections, i.e. injectate that is delivered from the needle free injector, through the skin and into subcutaneous tissue.

BACKGROUND OF THE INVENTION

For many conditions, injection of indicated medication can occur at home. Many patients, however, are needle-averse or suffer from needle-phobia, and/or have other difficulties including inability or lack of desire to follow complex instructions, fear of self administration, and danger of needle stick injury and cross contamination. Ensuring treatment compliance can be problematic. In addition, it is a problem that patients may need to be trained to self administer an injection, although for some indications the number of injections they would self administer is only a few. In addition, a needle and syringe in general needs to be filled, and for some formulations the drug is dried and requires reconstitution, which further complicates self administration and reduces compliance. These issues often rule out the possibility of treatment in a home setting, either self treatment or by a relatively un-trained care giver such as a family member. The inability to dose at home can lead to higher costs of therapy, delay in treatment, reduced compliance, reduced comfort, and potential exposure to hospital acquired infections.

Some issues are particularly acute in the context of elevated viscosity formulations, including but not limited to controlled release formulations, and formulations of biologic drugs, such as Monoclonal Antibodies (MABs). Elevated viscosity leads to many delivery difficulties, such as high required hand strength for a needle and syringe, long delivery times, and additional pain and fear associated with a large bore needle. Thus there is a need to deliver these compounds without a needle, preferably in a rapid, automated fashion using a system that does not require filling, reconstitution, or other complex procedures.

A dosage form that is easy and fast to self administer can be crucial for acute, debilitating conditions, for example small molecules such at triptans for migraine and cluster headache, or glucagon, a polypeptide for the acute treatment of hypoglycemia. Oral drugs have the advantage that they are easy to self administer. However, many drugs, especially peptide and protein drugs have very limited oral bioavailability, due to digestion and first pass liver metabolism. Additionally, absorption following oral delivery is delayed, with time to peak plasma concentrations ($T_{max}$) of ~40 minutes or longer.

It is known that needle free injectors can address the issues above of patient needle-phobia, compliance with therapy, needle stick injury, and cross contamination. However, it is important that the design parameters, such as the pressure in the drug container, the size of the injection orifice or orifi, and the pressure profile during delivery, be properly chosen to ensure successful injection. Improper choice of parameters can lead to problems such as wet (incomplete) injection, or at the other extreme too deep, for example intra-muscular, injection.

Needle-free injectors are available using many different types of energy sources, and the energy may be supplied by the user, for example where a spring is manually compressed and latched to temporarily store the energy until it is required to actuate the injector. Alternatively, the injector may be supplied having the energy already stored—for instance by means of a pre-compressed spring (mechanical or compressed gas), or by pyrotechnic charge.

Some injectors are intended for disposal after a single use, whereas others have a re-loadable and/or multi-dose energy storage means and a single or multi-dose medicament cartridge, and there are many combinations to suit particular applications and markets. For the purposes of the present disclosure, the term "actuator" will be used to describe the energy storage and release mechanism, whether or not it is combined with a medicament cartridge. In all cases, it is necessary to arrange for sufficient force at the end of the delivery to deliver the entire dose of medicament at the required pressure.

EP 0 063 341 and EP 0 063 342 disclose a needle-free injector which includes a piston pump for expelling the liquid to be injected, which is driven by a motor by means of a pressure agent. The liquid container is mounted laterally to the piston pump. The amount of liquid required for an injection is sucked into the pump chamber by way of an inlet passage and a flap check valve when the piston is retracted. As soon as the piston is moved in the direction of the nozzle body the liquid is urged through the outlet passage to the nozzle and expelled. The piston of the piston pump is a solid round piston.

EP 0 133 471 describes a needle-free vaccination unit which is operated with carbon dioxide under pressure, from a siphon cartridge by way of a special valve.

EP 0 347 190 discloses a vacuum compressed gas injector in which the depth of penetration of the injected drug can be adjusted by means of the gas pressure and the volume of the drug can be adjusted by way of the piston stroke.

EP 0 427 457 discloses a needle-free hypodermic syringe which is operated by means of compressed gas by way of a two-stage valve. The injection agent is disposed in an ampoule which is fitted into a protective casing secured to the injector housing. The ampoule is fitted on to the end of the piston rod. Disposed at the other end of the ampoule is the nozzle whose diameter decreases towards the end of the ampoule.

WO 89/08469 discloses a needle-free injector for one-time use. WO 92/08508 sets forth a needle-free injector which is designed for three injections. The ampoule containing the drug is screwed into one end of the drive unit, with the piston rod being fitted into the open end of the ampoule. At its one end, the ampoule contains the nozzle through which the drug is expelled. A displaceable closure plug is provided approximately at the center of the length of the ampoule. The dose to be injected can be adjusted by changing the depth of the ampoule. The piston rod which projects from the drive unit after actuation of the injector is pushed back by hand. Both units are operated with compressed gas.

WO 93/03779 discloses a needle-free injector with a two-part housing and a liquid container which is fitted laterally to the unit. The drive spring for the piston is stressed by means of a drive motor. The spring is released as soon as the two parts of the housing are displaced relative to each other by pressing the nozzle against the injection location. Respective valves are provided in the intake passage for the liquid and in the outlet of the metering chamber.

WO 95/03844 discloses a further needle-free injector. It includes a liquid-filled cartridge which at one end includes a nozzle through which the liquid is expelled. At the other end the cartridge is closed by a cap-type piston which can be pushed into the cartridge. A piston which is loaded by a pre-stressed spring, after release of the spring, displaces the cap-type piston into the cartridge by a predetermined distance, with the amount of liquid to be injected being expelled in that case. The spring is triggered as soon as the nozzle is pressed sufficiently firmly against the injection location. This injector is intended for one-time or repeated use. The cartridge is arranged in front of the spring-loaded piston and is a fixed component of the injector. The position of the piston of the injector which is intended for a plurality of uses is displaced after each use by a distance in a direction towards the nozzle. The piston and the drive spring cannot be reset. The pre stressing of the spring is initially sufficiently great to expel the entire amount of liquid in the cartridge all at once. The spring can only be stressed again if the injector is dismantled and the drive portion of the injector assembled with a fresh, completely filled cartridge.

U.S. Pat. No. 5,891,086 describes a needle-free injector, combining an actuator and a medicament cartridge. The cartridge is pre-filled with a liquid to be injected in a subject, and having a liquid outlet and a free piston in contact with the liquid, the actuator comprising an impact member urged by a spring and temporarily restrained by a latch means, the impact member being movable in a first direction under the force of the spring to first strike the free piston and then to continue to move the piston in the first direction to expel a dose of liquid through the liquid outlet, the spring providing a built-in energy store and being adapted to move from a higher energy state to a lower energy state, but not vice versa. The actuator may comprise trigger means to operate the said latch, and thus initiate the injection, only when a predetermined contact force is achieved between the liquid outlet of the said cartridge and the subject.

In U.S. Pat. No. 3,859,996, Mizzy discloses a controlled leak method to ensure that the injector orifice is placed correctly at the required pressure on the subject's skin at the correct normal to the skin attitude. When placement conditions are met, controlled leak is sealed off by contact pressure on the subject's skin, the pressure within the injector control circuit rises until a pressure sensitive pilot valve opens to admit high pressure gas to drive the piston and inject the medicament.

In WO Patent 82/02835, Cohen and Ep-A-347190 Finger, disclose a method to improve the seal between the orifice and the skin and prevent relative movement between each. This method is to employ a vacuum device to suck the epidermis directly and firmly onto the discharge orifice. The discharge orifice is positioned normal to the skin surface in order to suck the epidermis into the orifice. This method for injection of the medicament into the skin and the injector mechanism are different and do not apply to the present invention because of its unique ampoule design.

In U.S. Pat. No. 3,859,996 Mizzy discloses a pressure sensitive sleeve on the injector which is placed on the subject, whereby operation of the injector is prevented from operating until the correct contact pressure between orifice and the skin is achieved. The basic aim is to stretch the epidermis over the discharge orifice and apply the pressurized medicament at a rate which is higher than the epidermis will deform away from the orifice.

In U.S. Pat. No. 5,480,381, T. Weston discloses a means of pressuring the medicament at a sufficiently high rate to pierce the epidermis before it has time to deform away from the orifice. In addition, the device directly senses that the pressure of the discharge orifice on the subject's epidermis is at a predetermined value to permit operation of the injector. The device is based on a cam and cam follower mechanism for mechanical sequencing, and contains a chamber provided with a liquid outlet for expelling the liquid, and an impact member, to expel the liquid.

In U.S. Pat. No. 5,891,086, T. Weston describes a needle-free injector that contains a chamber that is pre-filled with a pressurized gas which exerts a constant force on an impact member in order to strike components of a cartridge and expulse a dose of medicament. This device contains an adjustment knob which sets the dose and the impact gap, and uses direct contact pressure sensing to initiate the injection. Further examples and improvements to this needle-free injector are found in U.S. Pat. No. 6,620,135, U.S. Pat. No. 6,554,818, U.S. Pat. No. 6,415,631, U.S. Pat. No. 6,409,032, U.S. Pat. No. 6,280,410, U.S. Pat. No. 6,258,059, U.S. Pat. No. 6,251,091, U.S. Pat. No. 6,216,493, U.S. Pat. No. 6,179,583, U.S. Pat. No. 6,174,304, U.S. Pat. No. 6,149,625, U.S. Pat. No. 6,135,979, U.S. Pat. No. 5,957,886, U.S. Pat. No. 5,891,086, and U.S. Pat. No. 5,480,381, incorporated herein by reference.

A number of biologically-active agents in viscous formulations would benefit from being delivered using the needle-free injector. This group could consist of (but not limited to) anti-inflammatory agents, antibacterial agents, antiparasitic agents, antifungal agents, antiviral agents, anti-neoplastic agents, analgesic agents including opioids, drugs for the treatment of arthritis including rheumatoid arthritis, antibodies, including monoclonal antibodies, protein and peptide drugs, including recombinant proteins and peptides, antipsychotics, anesthetics, vaccines, central nervous system agents, growth factors, hormones, antihistamines, osteoinductive agents, cardiovascular agents, anti-ulcer agents, bronchodilators, vasodilators, birth control agents and fertility enhancing agents, interferon alpha, growth hormone, osteoporosis drugs including PTH and PTH analogs and fragments, obesity drugs, psychiatric drugs, anti-diabetes, female infertility, AIDS, treatment of growth retardation in children, hepatitis, multiple sclerosis, migraine headaches, and allergic reactions.

SUMMARY OF THE INVENTION

An aspect of the invention is a method of delivering a formulation from a needle free injector, comprising:

actuating a needle free injector to pressurize a liquid formulation and cause the formulation to be injected through an orifice of the injector;

continuing to pressurize the formulation to create a pressure profile vs. time curve after actuation which curve comprises a skin puncture phase comprising a main pressure peak with a maximum pressure; and further continuing to pressurize the formulation through a delivery phase following the skin puncture phase which delivery phase occurs at a lower pressure compared to the maximum pressure of the main pressure peak, the delivery phase characterized by a delivery time per 0.5 mL of injectate per orifice, wherein the delivery time and the peak pressure are chosen to satisfy the relationship:

$$17.4 * MPP(MPa) - TotIT0.5(ms/0.5\ ml) \geq 363.2$$

wherein TotIT$_{0.5}$ represents total injection time measured in milliseconds per 0.5 milliliters of formulation delivered per orifice and MPP represents peak pressure measured in MPa of the main peak of the puncture phase.

Another aspect of the invention is the method wherein an average pressure reached during the delivery phase is between 2.5 and 4.0 times less than the maximum pressure of the main pressure peak.

Another aspect of the invention is the method wherein the average pressure reached during the delivery phase is between 2.5 and 3.2 times less than the maximum pressure of the main pressure peak.

Another aspect of the invention is the method wherein the delivery time and the peak pressure are chosen to satisfy the relationship:

$$17.4*MPP(MPa)-TotIT_{0.5}(ms/0.5\ ml) \geq 554.9.$$

Another aspect of the invention is the method wherein the delivery time per 0.5 mL per orifice is less than 200 ms.

Another aspect of the invention is the method wherein the delivery time per 0.5 mL per orifice is less than 100 ms.

Another aspect of the invention is the method wherein the delivery time per 0.5 mL per orifice is less than 60 ms.

Another aspect of the invention is the method wherein the delivery time per 0.5 mL per orifice is greater than 35 ms.

Another aspect of the invention is the method wherein the target delivered volume is 1.0 mL.

Another aspect of the invention is the method wherein the target delivered volume is greater than 1.0 mL.

Another aspect of the invention is a needle free injector wherein a liquid formulation is pressurized to cause needle free injection through at least one orifice, wherein the injector is configured such that upon actuation the injector generates a pressure profile vs. time curve comprising a puncture phase including a main pressure peak with a maximum pressure, wherein the injector is further configured to provide a delivery phase following the puncture phase which occurs at a lower pressure than the maximum pressure of the main pressure peak, characterized by a delivery time per 0.5 mL of injectate per orifice, wherein the delivery time and the peak pressure are chosen to satisfy the relationship:

$$17.4*MPP(MPa)-TotIT_{0.5}(ms/0.5\ ml) \geq 363.2$$

wherein TotIT$_{0.5}$ is measured in ms, and MPP is measured in MPa.

Another aspect of the invention is the injector configured such that upon actuation the pressure in the formulation is relatively constant during the delivery phase.

Another aspect of the invention is the injector configured such that upon actuation the pressure in the formulation is slowly decreasing during the delivery phase.

Another aspect of the invention is the injector configured such that upon actuation the highest pressure during the delivery phase is less than ½ that of the maximum pressure of the main pressure peak.

Another aspect of the invention is the injector configured such that upon actuation the highest pressure during the delivery phase is less than ⅓ that of the maximum pressure of the main pressure peak.

Another aspect of the invention is the injector configured such that upon actuation the average pressure during the delivery phase is between 2.5 and 4.0 times less than the maximum pressure of the main pressure peak.

Another aspect of the invention is the injector configured such that upon actuation the average pressure during the delivery phase is between 2.5 and 3.2 times less than the maximum pressure of the main pressure peak Another aspect of the invention is the injector configured such that upon actuation the delivery time and the peak pressure are chosen to satisfy the relationship:

$$17.4*MPP(MPa)-TotIT_{0.5}(ms/0.5\ ml) \geq 554.9.$$

Another aspect of the invention is the injector configured such that upon actuation the maximum pressure of the main pressure peak is between 35 and 40 MPa.

Another aspect of the invention is the injector configured such that upon actuation the delivery time per 0.5 mL per orifice is less than 200 ms.

Another aspect of the invention is the injector configured such that upon actuation the delivery time per 0.5 mL per orifice is less than 100 ms Another aspect of the invention is the injector configured such that upon actuation the delivery time per 0.5 mL per orifice is less than 60 ms.

Another aspect of the invention is the injector configured such that upon actuation the delivery time per 0.5 mL per orifice is greater than 35 ms.

Another aspect of the invention is the injector configured such that upon actuation the target delivered volume is 0.5 mL.

Another aspect of the invention is the injector configured such that upon actuation the target delivered volume is 1.0 mL.

Another aspect of the invention is the injector configured such that upon actuation the target delivered volume is greater than 1.0 mL.

An objective of the invention is to provide a method for delivering injectable therapeutics that limits the possibility of needle stick and cross contamination, for example with the HIV virus; improves patient compliance; and improves efficacy of drug delivery.

The invention is preferably carried out using a needle-free injector. More preferably, the invention is carried out utilizing a pre-filled, self contained, single use, portable needle free injector In a particularly preferred embodiment, the invention is carried out using a needle free injector that is powered by a self contained compressed gas charge, elements of which are described in U.S. Pat. No. 5,891,086 (incorporated by reference in its entirety). This embodiment includes a device for delivering formulations by needle-free injection, for example Subcutaneously (SC), Intra-Dermally (ID) or Intra-Muscularly (IM). An actuator is used in conjunction with a drug cartridge to form a needle-free injector. The cartridge is pre-filled with a liquid to be injected in a subject, the cartridge having at least one liquid outlet and a free piston inward of the liquid outlet in contact with the liquid.

The actuator comprises:

(a) a housing having a forward portion adapted to be connected with the cartridge;

(b) impact member mounted within said housing inward of the forward portion so as to be movable from a first position toward the forward portion to strike the free piston when a cartridge is connected and to continue to move the free piston toward the liquid outlet whereby a dose of the liquid is expelled through the liquid outlet in the cartridge;

(c) an element within said housing which engages said impact member to prevent movement of the impact member, wherein upon actuation the element allows movement of the impact member.

The current invention describes various formulations that can be delivered using a needle-free injector including the injector of U.S. Pat. No. 5,891,086. These formulations active ingredients, and may include various polymers, carriers, etc.

An aspect of the invention is a desirable delivery time, especially for high viscosity formulations. Desirable delivery times may include any delivery times wherein the formulation is successfully delivered. Preferred delivery times include those less than the reaction time of a human, for example less than ~600 ms per 0.5 mL of formulation delivered, more preferably less than 100 ms/0.5 mL.

Another aspect of the invention is acceptable pain associated with injection.

Another aspect of the invention relates to alleviation of fear of needles associated with injection of formulations.

Another aspect of the invention relates to the elimination of the danger of needle stick injury and cross-contamination associated with injection of formulations.

Another aspect of the invention relates to the simplification of preparation associated with injection of formulations, by supplying a pre-filled, single use disposable injector.

Another aspect of the invention relates to the drug release profile associated with injection of high viscosity depot formulation, especially surface eroding systems.

It is an aspect of the invention to achieve a rate of incomplete (wet) injections that is below a pre-selected level. More specifically, it is an aspect of the invention to ensure that injection reliability is such that a suitable percentage of the patient population being treated achieves the goal or goals of the therapy by ensuring at least a predetermined level of success.

It is another aspect of the invention to supply a model that can be used to reliably predict the rate of wet injections, such that it can be used to constrain the design of the needle free injector.

It is a further aspect of the invention to supply an in-vitro/in-vivo correlation (IVIVC) capable of ensuring that design changes to a needle free injector will not result in a loss of efficacy in-vivo, without requiring additional clinical trials.

A further aspect of the invention is a needle free injector with design elements that are consistent with a rate of wet injections below a pre-selected level.

A further aspect of the invention is a needle free injector that achieves a rate of wet injections below a pre-selected level.

A further aspect of the invention is a needle free injector with an acceptable rate of wet injection. In a preferred embodiment, the needle-free injector delivers 90% or more of the target dose of injectate in-vivo. More specifically, wherein the acceptable rate is defined as 95% confidence that 95% or more of the injections result in 90% or more of the target amount of drug delivered to the subcutaneous tissue of the subject.

These and other objects, advantages, and features of the invention will become apparent to those persons skilled in the art upon reading the details of the formulations and methodology as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 6 is a tabulation of the configurations of an embodiment of the current invention used in the development and validation of the IVIVC. Specifically, configuration 400 was used in a human clinical trial (the CPV trial) that was used to validate the IVIVC.

FIG. 9 is an ANOVA table for the gas mass and orifice size model, as described in Example 2.

FIG. 10 shows the results of a confirmation of the pressure and orifice model described in Example 2.

DETAILED DESCRIPTION OF THE INVENTION

Figure 1:
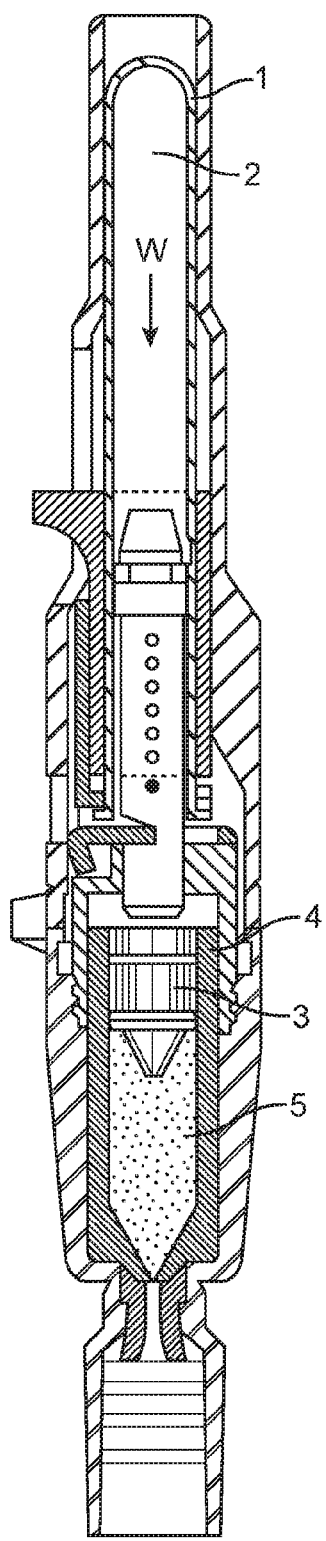
FIG. 1 is a cross-sectional view of one embodiment of the invention, a needle free injector optimized using the current invention.

Before the present formulations and methods are described, it is to be understood that this invention is not limited to particular formulations and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

Active Pharmaceutical Ingredient, API, active drug substance, medicament, or the like: A component of a pharmaceutical formulation that is pharmaceutically active and is delivered for a desired effect.

Actuator: A mechanical device for moving or controlling a mechanism or system. An example of an actuator is a lever that a patient uses to ready an auto-injector for delivery. Alternatively, an actuator can refer to the mechanical portion of an auto-injector that comprises an energy store, and may include a safety that must be set prior to delivery, a trigger for the device, and ensures the proper pressure profile during delivery.

Aggregation: formation of linked molecules held together by Van der Waals forces or chemical bonds.

AUC: Area under the curve, or the integral, of the plasma concentration of delivered drug over time Biodegradable: capable of chemically breaking down or degrading within the body to form nontoxic components. The rate of degradation of a depot can be the same or different from the rate of drug release.

Biologic: A medicinal products created by biological processes (as opposed to chemically). Examples include vaccines, blood and blood components, allergenics, somatic cells, gene therapy, tissues, stem cells, immune globulins, and recombinant therapeutic proteins. Biologics may be isolated from natural sources such as humans, animals, plants, or microorganisms—or may be produced by biotechnology methods.

Bulk erosion: The rate of water penetration into the depot exceeds the rate at which the depot is eroded (i.e. transformed into water soluble products)—leading to an erosion process that occurs throughout the entire volume of the depot—characteristic of most hydrophilic polymers used in drug delivery currently.

Carrier: a non-active portion of a formulation which may be a liquid and which may act as a solvent for the formulation, or wherein the formulation is suspended. Useful carriers do not adversely interact with the active pharmaceutical ingredient and have properties which allow for delivery by injection, specifically needle free injection. Preferred carriers for injection include water, saline, and mixtures thereof. Other carriers can be used provided that they can be formulated to create a suitable formulation and do not adversely affect the active pharmaceutical ingredient or human tissue.

Centipoise and centistokes: different measurements of viscosity, which are not just different units. Centipoise is a dynamic measurement of viscosity whereas centistokes is a kinematic measurement of viscosity. The conversion from centistokes and centipoise to S.I. units is given below:

$$1 \text{ cS} = 0.0001 \text{ m}^2/\text{s} \quad 1 \text{ cP} = 0.001 \text{ Ns/m}^2$$

Coefficient of Thermal Expansion, Thermal Expansion Coefficient, and the like: The fractional change in size of a material ($\Delta L/L$), per degree C.

Coefficient of Friction: a constant of proportionality relating the normal force between two materials, and the frictional force between those materials. Generally friction is considered to be independent of other factors, such as the area of contact. The coefficient of static friction characterizes the frictional force between two materials when at rest. This force is generally what is required to start relative movement. The coefficient of dynamic friction characterizes the frictional force between to materials that are moving relative to one another. In general, the coefficient of static friction is higher than the coefficient of dynamic friction.

Container Closure, Container Closure System, and the like: A drug container that is designed to maintain sterility and eliminate the possibility of contamination of the drug formulation. For container closure systems that contain liquid formulations, the container closure system must also have sufficiently low vapor transmission rate such that the concentration of the formulation does not change appreciably over the product shelf life. Preferred materials have sufficiently low leachable materials such that they do not contaminate the formulation during storage. Preferred materials for container closures include glass, more preferably boro-silicate glass, or fluorinated materials such as polytetrafluoroethylene (PTFE).

Container Closure Integrity: The ability of a container closure system to maintain sterility, eliminate the possibility of contamination, and minimize loss of carrier during storage.

CPV trial: a 400 subject trial used to validate the predictive power of the IVIVC of the present invention.

Figure 2:
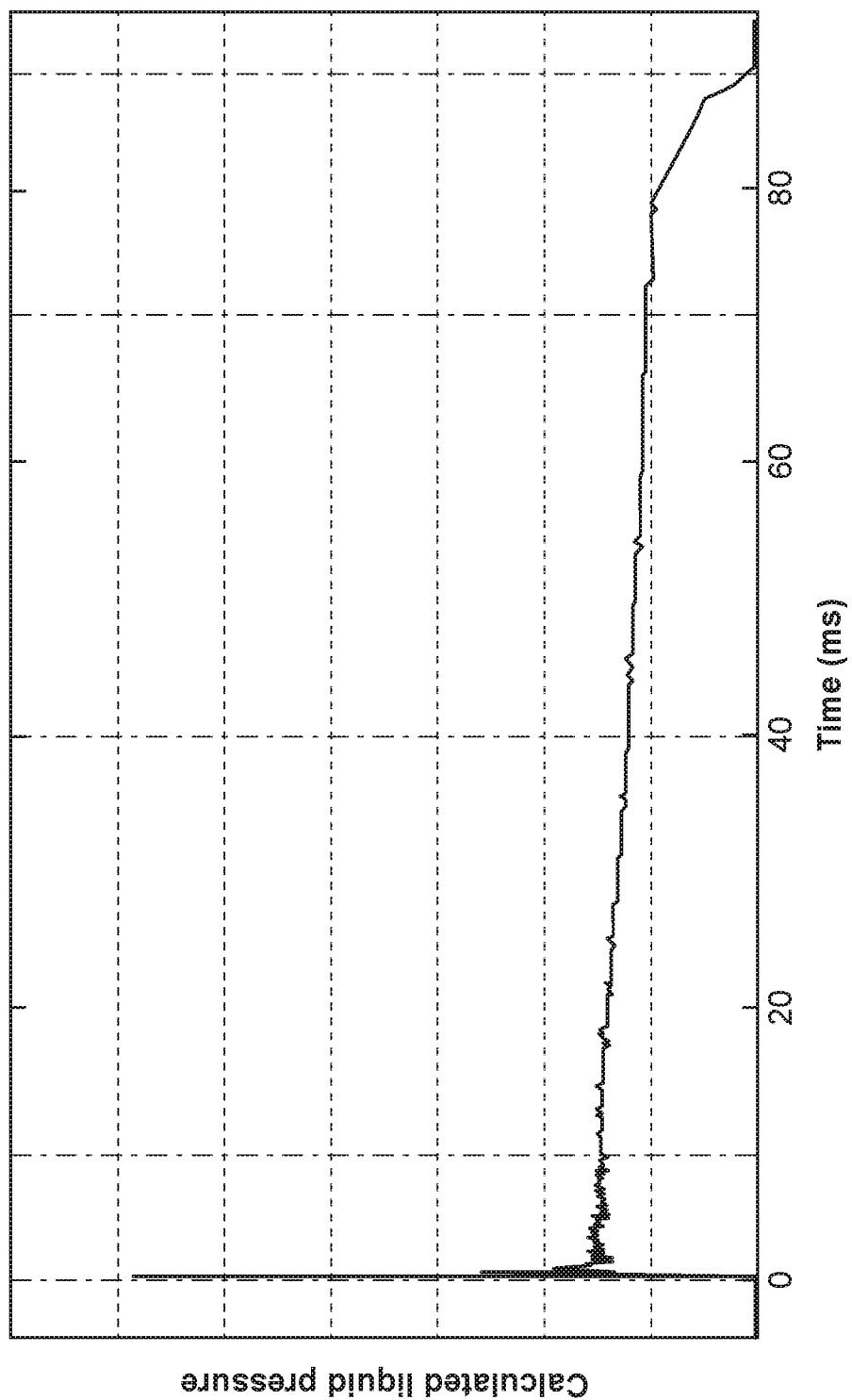
FIG. 2 is a graph of the formulation pressure vs. time using one version of the device of FIG. 1.

Delivery Phase: A constant or slowly varying formulation pressure during which the bulk of a formulation dose is delivered from a needle-free injector (see FIG. 2). In a preferred embodiment of the current invention, the desired injection is a subcutaneous injection. This in general requires a previous, higher pressure phase (see "puncture phase") wherein the hole through which the injectate is delivered is formed.

Depot Injection, Depot, and the like: an injection, usually subcutaneous, intravenous, or intramuscular, of a pharmacological agent which releases its active compound in a consistent way over a long period of time. Depot injections may be available as certain forms of a drug, such as decanoate salts or esters. Examples of depot injections include Depo Provera and haloperidol decanoate. Depots can be, but are not always, localized in one spot in the body.

DosePro, or Intraject: a single use, prefilled, disposable, needle free injector currently manufactured by Zogenix Corporation. A cartridge is pre-filled with a liquid to be injected in a subject, and having a liquid outlet and a free piston in contact with the liquid, the actuator comprising an impact member urged by a compressed gas spring and temporarily restrained until the device is actuated, the impact member being movable in a first direction under the force of the spring to first strike the free piston and then to continue to move the piston in the first direction to expel a dose of liquid through the liquid outlet, the spring providing a built-in energy store and being adapted to move from a higher energy state to a lower energy state, but not vice versa. The actuator may comprise a trigger means to actuate the device, and thus initiate the injection, only when the device is pressed against the skin. Elements and variations of DosePro are described in U.S. Pat. No. 5,891,086, and additional description, improvements, and variants can be found in U.S. Pat. No. 6,620,135, U.S. Pat. No. 6,554,818, U.S. Pat. No. 6,415,631, U.S. Pat. No. 6,409,032, U.S. Pat. No. 6,280,410, U.S. Pat. No. 6,258,059, U.S. Pat. No. 6,251,091, U.S. Pat. No. 6,216,493, U.S. Pat. No. 6,179,583, U.S. Pat. No. 6,174,304, U.S. Pat. No. 6,149,625, U.S. Pat. No. 6,135,979, U.S. Pat. No. 5,957,886, U.S. Pat. No. 5,891,086, and U.S. Pat. No. 5,480,381, incorporated herein by reference. Although many delivery systems and techniques may be used with the current invention, DosePro is the preferred method.

Excipient: Any substance, including a carrier, added to an active drug substance to permit the mixture to achieve the appropriate physical characteristics necessary for effective delivery of the active drug.

Filter Paper Weight, or FPW: a measure of the amount of injectate left on the skin after a needle free injection event. To measure FPW, the non-injected material is absorbed onto filter paper, the sample is weighed, and the tare weight subtracted. If blood is seen in the sample, this is noted, and in general the results are not used as the blood will cause an overestimate of the FPW. The FPW can be used to calibrate and correct the VAS, see definition of VAS and example 1.

Formulation, Injectate, and the like: Any liquid, solid, or other state of matter that can be injected. Preferred formulations are liquid formulations, including but not limited to solutions, suspensions including nano-suspensions, emulsions, polymers and gels. Formulations include but are not limited to those containing Excipient that are suitable for injection, and contain one or more active pharmaceutical ingredients.

Immunogenicity: The ability of a substance (an antigen) to provoke an immune response. Aggregated biologic drugs can be immunogenic even when the unaggregated molecule is not immunogenic.

Impact gap, slap-hammer distance, and the like: The width of a gap between an impact member and a piston used to create a slap hammer effect, i.e. a pressure spike in the formulation. During a needle free delivery event, the impact member is urged across the gap, for example by compressed gas or another energy source, wherein it integrates the work done by the energy source as it travels across the gap, and delivers this energy to the formulation upon impact, creating an early pressure spike. See also "Puncture Phase".

In-vivo (from the Latin for "within the living"): Experimentation using a whole, living organism as opposed to a partial or dead organism, or an in-vitro experiment. In-vivo research includes animal testing and human clinical trials. In-vivo testing is often preferred over in-vitro testing because the results may be more predictive of clinical results In-vitro (from the Latin for within the glass): A procedure not in a living organism (see in-vivo) but in a controlled environment, such as in a test tube or other laboratory experimental apparatus. In-vitro testing is often preferred over In-vivo testing due to reduced cost and reduced danger to human and/or animal subjects.

In-vivo/In-vitro correlation, IVIVC, and the like: a model, preferably a mathematical model, that predicts In-vivo performance based on In-vitro measurements, design parameters, and the like. A predictive IVIVC allows the predictive value of in-vivo measurements without the need for expensive and potentially dangerous human or animal clinical trials. An IVIVC is preferably based on a meta-analysis of several clinical, preferably human, trials utilizing different configurations of a drug, drug delivery technology, or other medical device technology. For the sake of this discussion, and IVIVC can be taken to mean a model that predicts in-vivo injection performance of a needle free injector based on injector design parameters and bench measurements of performance.

Figure 4:
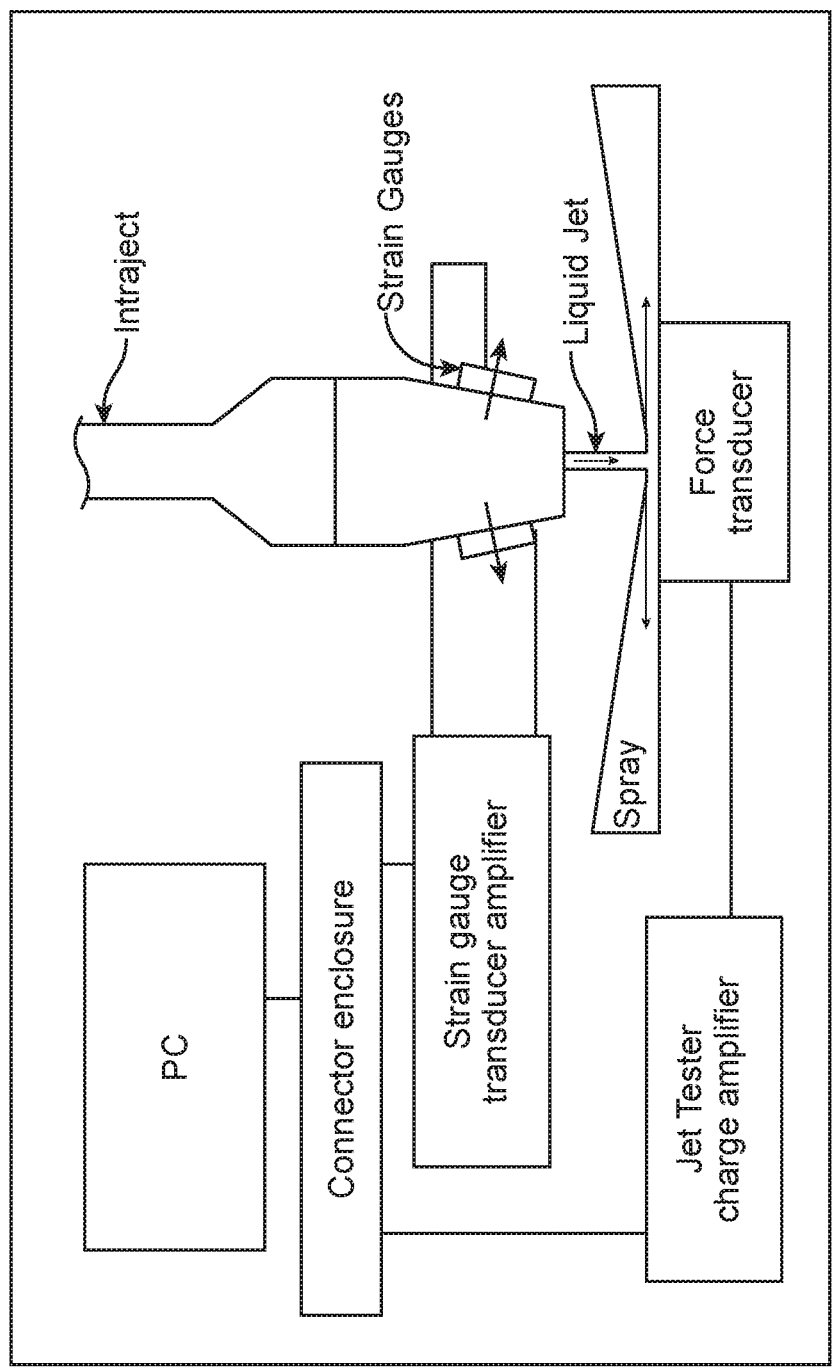
FIG. 4 is a schematic diagram of a "Jet Tester" that measures various parameters including drug formulation pressure and jet velocity during an in-vitro delivery event.
Figure 5:
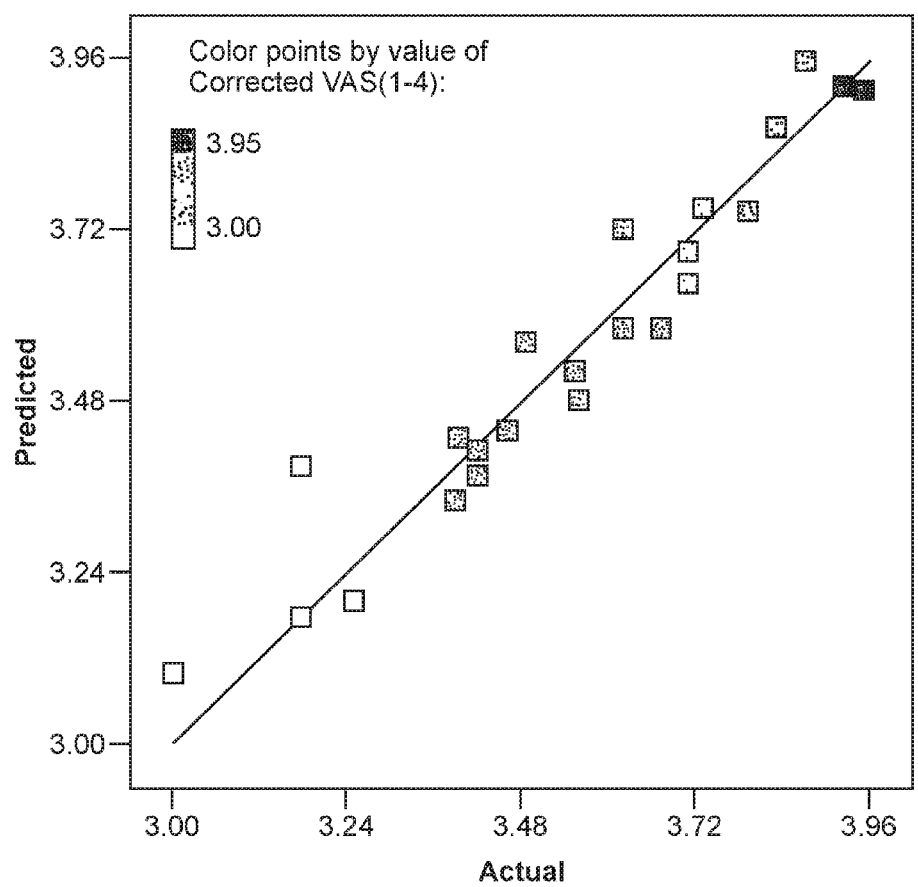
FIG. 5 is a graph of actual Visual Assessment Score (VAS) vs. the VAS predicted by using the method of the invention.

Jet Test, Jet Tester, Jet Test Method, and the like: a benchtop apparatus that measures the force on a transducer when impinged upon by the liquid jet during a simulated drug delivery event. Using these data the formulation pressure over time can be calculated. The Jet Test is often conducting simultaneously with the Strain Gauge test. FIG. 4 is a schematic of the Jet Tester used in the development of the current invention.

Needle free Injector, Needle-less injector, Jet Injector, and the like: a drug delivery system which delivers a subcutaneous, intramuscular, or intradermal injection without the use of a hypodermic needle. Injection is achieved by creating at least one high velocity liquid jet with sufficient velocity to penetrate the skin, stratum subcutaneum, or muscle to the desired depth. Needle free injection systems include, but are not limited to, the DosePro® system manufactured by Zogenix Corporation, the Bioject® 2000, Iject or Vitaject devices manufactured by Bioject Medical Technologies, Incorporated, the Mediject VISION and Mediject VALEO devices manufactured by Antares, the PenJet device manufactured by Visionary Medical, the CrossJect device manufactured by Crossject, the MiniJect device manufactured by Biovalve, the Implaject device manufactured by Caretek Medical, the PowderJect device manufactured by AlgoRx, the J-tip device manufactured by National Medical Products, the AdvantaJet manufactured by Activa Systems, the Injex 30 device manufactured by Injex-Equidyne, and the Mhi-500 device manufactured by Medical House Products.

Piston: a component of a needle free injector that under force from an energy source drives liquid formulation out of an orifice to achieve a needle free injection. In a preferred embodiment, the needle free injector is prefilled with formulation, and the piston then becomes a drug contact surface of the container-closure system. In a particularly preferred embodiment, the piston has the additional function of transmitting energy from an impact member to the formulation to create a pressure spike, see "Puncture Phase". Preferably, the piston comprises PTFE.

Polytetrafluoroethylene, PTFE, Teflon, and the like: a synthetic fluoropolymer of tetrafluoroethylene. PTFE is most well known by the DuPont brand name Teflon. PTFE is a high molecular weight fluorocarbon solid, consisting wholly of carbon and fluorine. PTFE has one of the lowest coefficients of friction against any solid.

Prophylaxis: The administration of a drug used to prevent the occurrence or development of an adverse condition or medical disorder.

Puncture Phase, Initial Pressure Spike, and the like: An initial spike in pressure in the formulation in a needle-free injector that creates a jet with sufficient energy to drill to the desired depth into or through the skin (see FIGS. 2 and 3). In a preferred embodiment of the invention, the injection is a subcutaneous injection. In order to achieve an efficient, reproducible subcutaneous injection, it is important that the jet be sufficiently energetic to drill down to the subcutaneum. However, it is then important that the bulk of the formulation be delivered at a lower pressure, in order that the formation of the hole is stopped prior to the injection becoming a painful intra-muscular injection.

Skinfold Thickness is a measure of the amount of subcutaneous fat, obtained by inserting a fold of skin into the jaws of a caliper. The skinfolds are generally measured on the upper arm, thigh or upper abdomen of a human patient.

Surface Erosion: The rate of water penetration into a depot is slower than the rate at which the depot is eroded—the depot erodes from the surface before water has penetrated the entire volume of the device.

Specific gravity: The ratio of a compound's density to that of water.

Spring: a mechanism capable of storing energy for use in propelling the medicament in the syringe into and through the patient's skin and into body, wherein the force provided by the energy store is proportional to a displacement. This mechanism may be mechanical, e.g. compressible metal component such as a coil spring or Belleville washer stack. Preferably, the mechanism is a compressed gas spring in which the energy is stored, and when released the gas expands.

Strain Gauge Test, Strain Gauge Method, and the like: A method of measuring the formulation pressure during an in-vitro delivery event, wherein a strain gauge is attached to the formulation container, calibrated for formulation pressure, and then used to measure the pressure profile over time of the formulation. The Strain Gauge Test is generally conducted in parallel with a Jet Test.

Subcutaneous tissue, stratum subcutaneum, hypodermis, hypoderm, or superficial fascia, and the like: A layer of tissue that lies immediately below the dermis of skin, consisting primarily of loose connective tissue and lobules of fat. The stratum subcutaneum is the target of a subcutaneous injection.

Successful Injection: an injection in which greater than 90% of the intended injection volume is delivered through the skin into the subcutaneous tissue.

Visual Assessment Score, VAS, and the like: A semi-quantitative method of scoring needle free injections on a scale of 0-4, based on observation. The visual assessment is calibrated by weighing the amount of injectate left on the skin, see "Filter Paper Weight" definition above. Any injection scored as a 0, 1 or 2 is termed unsuccessful (see "wet injection", below), while a 3 or 4 is a successful injection. Injection scores are defined as follows:

0=100% splash back of injectate, not even a hole in the epidermis

1=hole in the epidermis but very little, if any penetration of injectate

2=some penetration of injectate (~5% and <90%)

3=~90 and <95% penetration of injectate

4=~95% penetration of injectate

Water Vapor Transmission Rate (WVTR)) is the steady state rate at which water vapor permeates through a material. Values are expressed in $g/100\ in^2/24$ hr in US standard units and $g/m^2/24$ hr in metric units.

Wet injection: an unsuccessful needle free injection, whereby more than 10% of the injectate does not penetrate to the stratum subcutaneum. A related definition is an injection with a Visual Assessment Score (VAS) of less than 3.

INVENTION IN GENERAL

The use of a prefilled injector has many benefits over a standard needle and syringe, including:

No need to draw formulation into the syringe prior to use

Fewer steps

Simpler instructions

Minimal amount of equipment required (especially important for acute indications wherein the injector must be carried around by the user.)

Fast administration

Improved patient compliance

Improved disease outcomes.

Prefilled auto-injectors have additional advantages in that the energy for the delivery comes from the device rather than the patient or caregiver that is administering the medication. This can be very important, for example, in the delivery of high viscosity formulations that require high hand strength, long delivery times, and large needle gauges, when delivered utilizing a standard needle and syringe.

A preferred embodiment of the auto-injector is the needle-free injector. Needle-free injectors are preferred because of:

No danger of needle stick injury and related exposure to disease

No needle phobia

Small diameter liquid jets result in little or no pain sensation

No requirement for sharps disposal

Very short flow path (as compared to a hypodermic needle) that reduces viscous losses and enables delivery of high viscosity formulations.

Needle free injectors, while having these advantages over a needle and syringe or a standard auto-injector with a needle, in general have the disadvantage that the dynamics of the liquid as it exits the device determine the injection depth and quality, unlike standard injectors wherein the needle sets the depth of injection and if the injection is performed properly, essentially all of the injectate is delivered to the target region. Therefore it is critical to know how various design parameters and/or measured jet dynamic parameters can impact injection performance, and then control those parameters to ensure a suitable level of successful injections, specifically to ensure that there will be less than a pre-specified number of wet injections when the system is used in-vivo.

Needle free injectors have a number of parameters that can be modified, and may have impact on injection performance. These include the power source, which may be a compressed gas, pyrotechnic charge or charges, mechanical spring, or any other energy storage means. The strength of the power source, such as gas pressure and volume, pyrotechnic charge chemistry and amount of combustible material, or mechanical spring constant and pre-compression, may be important to performance Other parameters that may be of importance include but are not limited to: jet orifice diameter, number of orifi, hydraulic parameters such as orifice length and shape, formulation properties such as viscosity, and the mechanical properties of the actuator, i.e. how it converts energy from the power source into formulation pressure, more specifically the pressure profile vs. time during the delivery event.

In a preferred embodiment, the needle free injector includes an impact member that is separated from a piston, which piston is in contact with a liquid drug formulation. When the device is triggered (preferably by pressing against the target skin region), energy from a compressed gas power source is transferred to the impact member as work done by the gas in expansion as the impact member traverses the gap. This creates a "slap hammer" effect whereby a pressure spike in the formulation is created when the impact member strikes the piston. This pressure spike creates a very energetic liquid jet that creates a hole in the epidermis to the desired depth, preferably the subcutaneum (the "puncture phase"). The pressurized gas then continues to urge the impact member, and thus the piston, forward, delivering the formulation through the hole and into the subcutaneous tissue (the "delivery phase") at a lower pressure that holds the hole open and delivers the dose, but does not continue increasing the depth of the hole. In this way, a repeatable subcutaneous injection is achieved while avoiding a painful intra-muscular injection. Control of the size of the gap, the force on the impact member, and potentially the mass of the impact member can all influence the rate of successful injection and the amount of injectate delivered.

It may be desirable or required to change these or other parameters during development, or post-regulatory approval, to improve such things as manufacturability, cost, reliability, or usability. However, it is very advantageous if these changes do not require extensive repeat of clinical trials to validate the change, due to the high expense and risk associated with clinical, and especially human clinical, trials. At a minimum it is desirable that the outcome of any required human clinical trial have a minimum risk associated with the quality of the needle-free injection. This requires a method of predicting the in-vivo performance impact of the changes, either by a model that directly predicts the in-vivo impact of device parameters, or preferably a model that correlates in-vitro, or laboratory benchtop experiments, or possibly a mixture thereof, with in-vivo performance. Such a model is referred to as an In-Vivo/In-Vitro Correlation, or IVIVC.

Such an IVIVC has been developed (see example 1 below). It was developed using the DosePro technology, as described in U.S. Pat. No. 5,891,086, and additional description and improvements can be found in U.S. Pat. No. 6,620,135, U.S. Pat. No. 6,554,818, U.S. Pat. No. 6,415,631, U.S. Pat. No. 6,409,032, U.S. Pat. No. 6,280,410, U.S. Pat. No. 6,258,059, U.S. Pat. No. 6,251,091, U.S. Pat. No. 6,216,493, U.S. Pat. No. 6,179,583, U.S. Pat. No. 6,174,304, U.S. Pat. No. 6,149,625, U.S. Pat. No. 6,135,979, U.S. Pat. No. 5,957,886, U.S. Pat. No. 5,891,086, and U.S. Pat. No. 5,480,381. In this model, a benchtop system (see FIG. 4) for measuring the formulation pressure profile over time was used to characterize a number of different configurations of the DosePro technology. These data were analyzed and compared to pre-existing in-vivo injection performance data utilizing these configurations, and a correlation was developed. The in-vivo performance was measured by a visual assessment by a trained observer of the amount of injectate left on the skin following delivery. This visual assessment technique has been validated by comparing the results to those measured directly by collecting the non-injected fluid on filter paper and weighing it.

Figure 3:
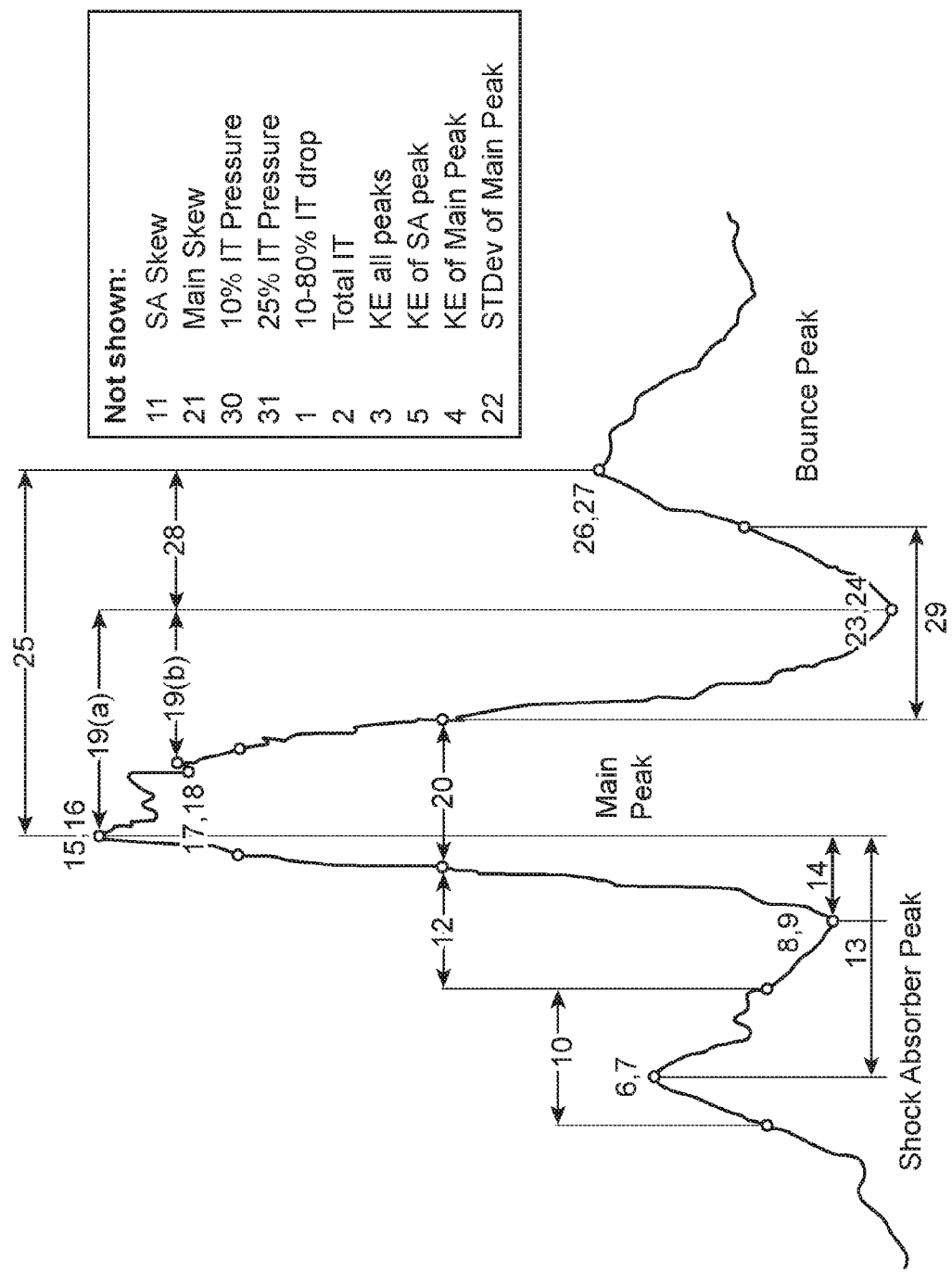
FIG. 3 is a graph showing an initial pressure spike of the "Puncture Phase" and showing parameters tested for correlation with injection performance.

The result of this work was the non-obvious and somewhat surprising result that the injection performance would be accurately predicted based on just two parameters, the height of the puncture phase formulation pressure peak created by the slap hammer effect described above, and the total injection time per 0.5 mL of formulation.

$$VAS = +1.1728 - 5.0305 \times 10^{-3} * (TotIT_{0.5}) + 0.0873 * (MPP)$$

where the $TotIT_{0.5}$ is the total injection time in ms per 0.5 mL of delivered formulation per orifice, and MPP is the peak pressure in MPa of the main peak of the puncture phase (see FIG. 3).

In a system where the gas pressure, orifice diameter, impact gap, and mass and hydraulic diameter of the impact member, at a minimum, would be expected to impact injection performance, it is an unexpected result, with high utility, that expected in-vivo performance can be predicted utilizing simply two parameters. Using this expression, it can be seen that if one designs a needle-free injector with a main peak pressure and an injection time per 0.5 mL of formulation such that $$+17.4*MPP(MPa) - TotIT_{0.5}(ms/0.5 \text{ mL}) \geq 363.2$$

it can be expected that wet injections will be avoided. The above expression assumes an average VAS of $\geq 3$, i.e. on average, greater than ~90% of the intended delivery volume will be injected.

Figure 7:
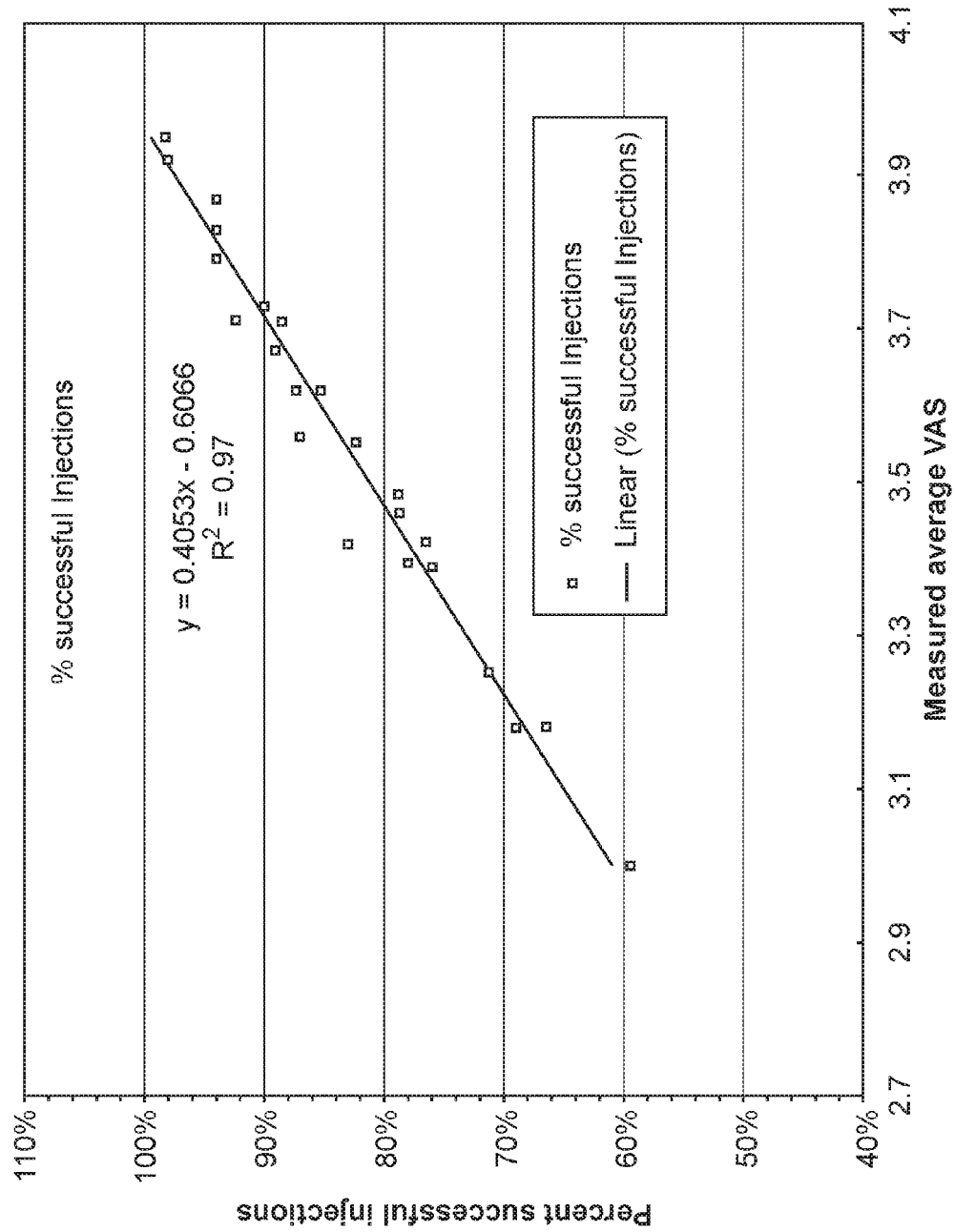
FIG. 7 is a graph showing the percentage of successful injectors vs. the measure average VAS.

However, an average VAS of $\geq 3$ may be considered unacceptable. As can be seen from FIG. 7, at an average VAS of 3, only 60% of injections are considered successful (successful injection defined as 90% of intended delivery volume injected). This is to be expected because the VAS is an average, and approximately 50% (exactly 50% if the data are Gaussian distributed) of the data will fall below that average. The best fit line (see FIG. 7) is:

$$FSI_{90} = 0.4053*VAS - 0.6066$$

Where $FSI_{90}$ is defined as the measured fraction of successful injections, where a successful injection is defined as 90% of the intended delivery volume injected. This expression can be inverted to give the required VAS to achieve a desired level of successful injections:

$$VAS = 2.4673*FSI_{90} + 1.4967.$$

Thus, if the fraction of successful injections desired is 0.9 (90%), the target VAS should be 3.71. Thus, it is preferable to have a needle free injector that satisfies the following:

$$+17.4*MPP(MPa) - TotIT_{0.5}(ms/0.5 \text{ mL}) \geq 505.4$$

It may be even more preferable to have 95% successful injections. This would require a target VAS of 3.84, i.e. a needle free injector that satisfies:

$$+17.4*MPP(MPa) - TotIT_{0.5}(ms/0.5 \text{ mL}) \geq 530.2$$

It is most preferable to have an expected 100% successful injections, which requires a VAS of $\geq 3.96$. Thus it is preferable to have a needle free injector that satisfies the following:

$$+17.4*MPP(MPa) - TotIT_{0.5}(ms/0.5 \text{ mL}) \geq 554.9$$

In order that a subcutaneous injection is achieved, and not a painful IM injection, it is important that the pressure during the delivery phase be less than that of the main peak pressure, as continuing to deliver at the pressure that will form a hole in the skin will mean the hole continues to be formed during the delivery phase. The pressure of the delivery phase should be less than ½ that of the puncture phase peak pressure, preferable less than ⅓ of the main peak pressure. It is preferred to have an average pressure during the delivery phase which is between 2.5 and 4.0 times less than the maximum pressure of the main pressure peak, more preferably between 2.5 and 3.2 times less. In one preferred embodiment, the maximum pressure of the main pressure peak is between 35 and 40 MPa, and the delivery time per 0.5 mL per orifice is less than 100 ms, preferably less than 60 ms, but it is preferred that the delivery time per 0.5 mL per orifice be greater than 35 ms.

In one preferred embodiment, the number of orifi is 1, and the target delivered volume is 0.5 mL. Another embodiment with 1 orifice has a target delivered volume 1.0 mL, preferably greater than 1.0 mL.

A detailed description of the work that led to this conclusion is in Example 1, below.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The primary objective was to create an IVIVC that is predictive and is not subject to the effects of subtle pressure profile variations that do not impact injection success. To create the IVIVC, configurations of the DosePro needle free injector were both studied in-vivo, using the Visual Assessment Score (VAS) and Filter Paper Weight (FPW) as response variables, and in-vitro, using the various measurements shown in FIG. 3. The FPW and the VAS have the following relationship:

FPW>475 mg~VAS1

FPW≤475 mg and FPW>50 mg~VAS2

FPW≤50 mg and FPW>25 mg~VAS3

FPW≤25 mg~VAS4

The FPW was used to correct the VAS as follows: If the FPW was smaller than would be indicated by the VAS, the VAS remained unchanged, the reasoning being that during poor injections, the injectate can spray away from the injection site, resulting in a lower than expected FPW. If the FPW was higher than would be indicated by the VAS, the VAS was revised downwards to correspond with the FPW. If blood was observed on the filter paper the VAS was not corrected, as there was no mechanism to correct for the weight of the blood. Of the injections studied in this work, the VAS was revised for less than 1%.

The configurations studied utilized the same materials and components, with variation in orifice diameter and gas charge. All configurations utilized the same impact gap.

To develop the IVIVC, the revised VAS was fit to the various measured pressure parameters shown in FIG. 3, and statistically significant correlations were used.

The acceptance criteria for a predictive IVIVC were as follows:

The model must utilize prior human clinical result to correctly predict performance in a subsequent human clinical trial (the so called "CPV" trial). By "correctly predict", it is meant that the model prediction interval must contain the performance for the CPV trial. Additionally, the IVIVC must have reasonable predictive abilities overall.

Predicted R-sq. statistic should be greater than 0.7, and within 0.20 of the adjusted R-sq. statistic.

The model must not incorrectly predict that a poor-performing configuration performs well and vice versa.

The model prediction interval of configuration 400 (see FIG. 6) must not contain the mean in-vivo performance of configuration 200, and vice versa.

The absolute value of the prediction error for all points in the model must be less than 15%.

The formulation pressure over time during a delivery event, for the different configurations tested, was determined two quite independent ways (see FIG. 4). During delivery, the liquid jet was made to impinge on a force transducer. This allowed measurement of jet momentum, and thus calculation of drug capsule pressure (the "Jet Test" method). Simultaneously, calibrated strain gauges attached to the glass drug capsule measured the formulation pressure measurement directly (the "Strain Gauge" method). Sample data are displayed in FIGS. 2 and 3.

The value of thirty-one in-vitro metrics was determined from the pressure traces (see FIG. 3), averages calculated for each configuration, and these were correlated with the corrected VAS. Of the thirty-one in-vitro metrics, two were used to develop this IVIVC, and are highlighted in FIG. 3. The two metrics used in the model were: 2—Total Injection Time per 0.5 mL per orifice (TotIT$_{0.5}$), and 15—Main Peak Pressure (MPP).

The model is:

$$\text{Corrected VAS}=+1.1728-5.0305\times10^{-3}*(\text{TotIT}_{0.5})+0.0873*(\text{MPP})$$

where the total injection time is in ms/(0.5 mL) and the Main Peak Pressure is in MPa.

While the predictive model outlined in Example 1 should be broadly applicable to needle free injectors, a more limited model that is specific to the type of needle free injector described in U.S. Pat. No. 5,891,086 (hereafter referred to as "DosePro") is also useful when set to operate with parameters described here. The best of these that was found was a correlation model that utilized only gas mass and orifice size. Both are device parameters that are specified as part of the manufacturing process, i.e. no experimental data is required to estimate system performance. Only patients with skin fold thickness greater than 10 mm were included in the analysis, as it has been previously shown that patients with skin fold thickness less than 10 mm have lower injection performance.

The model is:

$$\text{VAS}=-7.68811+13.22749*\text{Orifice Size}+0.10781*\text{Gas Mass}-17.18723*\text{Orifice Size}^2-3.19298E\text{-}004*\text{Gas Mass}^2$$

Where the Orifice Size is in mm, and the Gas Mass is in mg.

Figure 8:
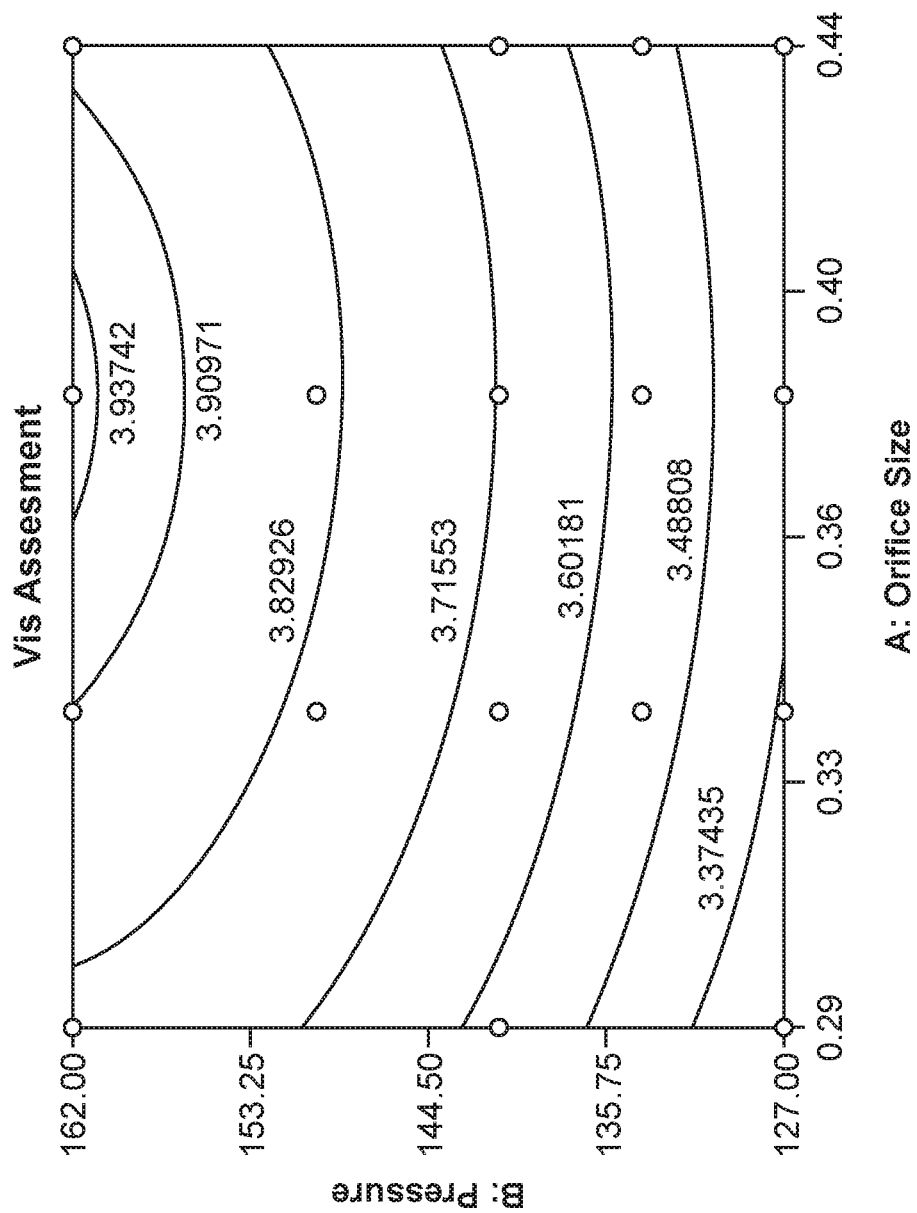
FIG. 8 is a graph showing the gas mass and orifice size model parameter space and prediction, as described in Example 2.

The model space is shown in FIG. 8. As the model is based on correlation, it is expected that the top only be valid within, or just outside, the parameter space for each input variable.

The ANOVA results from the correlation are shown in FIG. 9. The Model F-value of 46.69 implies the model is significant. There is only a 0.01% chance that a "Model F-Value" this large could occur due to noise. Values of "Prob>F" less than 0.0500 indicate model terms are significant. The "Fred R-Squared" of 0.8816 is in reasonable agreement with the "Adj R-Squared" of 0.9195. "Adeq Precision" measures the signal to noise ratio. A ratio greater than 4 is desirable. The ratio of 20.160 indicates an adequate signal.

The model was confirmed using clinical results that were not used in the development of the model. The configurations used and the results of the testing are shown in FIG. 10. These results confirm that the model is indeed predictive of DosePro clinical results.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A needle free injector wherein a liquid formulation is pressurized and extruded out of at least one orifice of the injector;
   wherein the injector is configured such that upon actuation the injector generates a pressure profile vs. time curve comprising a puncture phase including a main pressure peak with a maximum pressure,
   characterized by a delivery time per 0.5 mL of injectate per orifice, wherein the delivery time and the peak pressure are chosen to satisfy the relationship:

$$17.4*MPP(MPa)-TotIT_{0.5}(ms/0.5\ ml) >= 363.2$$

wherein $TotIT_{0.5}$ represents total injection time measured in milliseconds per 0.5 milliliter of formulation delivered per orifice, and MPP represents peak pressure and is measured in MPa.

2. The needle free injector of claim 1, wherein the delivery time and the peak pressure are chosen to satisfy the relationship:

$$17.4*MPP(MPa)-TotIT0.5(ms/0.5ml) >= 505.4.$$

3. The needle free injector of claim 1, wherein the delivery time and the peak pressure are chosen to satisfy the relationship:

$$17.4*MPP(MPa)-TotIT0.5(ms/0.5ml) >= 530.2.$$

4. The needle free injector of claim 2, further comprising an energy source selected from:
   a mechanical spring;
   a compressed gas;
   a pyrotechnic charge.

5. The needle free injector of claim 4, wherein the diameter of the at least one orifice is less than 1 mm and greater than 0.1 mm.

6. The needle free injector of claim 4, comprising multiple pyrotechnic charges.

7. The needle free injector of claim 5, wherein the main pressure peak is caused by an impact member which is urged across a gap by an energy source, and upon striking a piston, transfers much of the energy gained from the energy source into the formulation,
   further wherein due to the urging of the energy source, the impact member and the piston continue to move forcing the remainder of the delivered formulation out of the at least one orifice.

8. The needle free injector of claim 4, wherein the formulation is forced through two orifices of the injector.

9. The needle free injector of claim 5, wherein the needle free injector is a pre-filled, single use disposable injector.

10. The needle free injector of claim 4, wherein the formulation is selected from, controlled release formulations, and formulations of biologic drugs.

11. The needle free injector of claim 10, comprising monoclonal antibodies.

12. The needle free injector of claim 4, comprising a triptan.

13. The needle free injector of claim 3, wherein the formulation comprises:
    a biologically-active agent selected from anti-inflammatory agents, antibacterial agents, antiparasitic agents, antifungal agents, antiviral agents, anti-neoplastic agents, analgesic agents opioids, drugs for the treatment of arthritis drugs for the treatment of rheumatoid arthritis, antibodies, monoclonal antibodies, protein drugs, peptide drugs, antipsychotics, anesthetics, vaccines, central nervous system agents, growth factors, hormones, antihistamines, osteoinductive agents, cardiovascular agents, anti-ulcer agents, bronchodilators, vasodilators, birth control agents and fertility enhancing agents, interferon alpha, growth hormone, osteoporosis drugs PTH, PTH, obesity drugs, psychiatric drugs, anti-diabetes, treatments for female infertility, AIDS, growth retardation in children, hepatitis, multiple sclerosis, migraine headaches, and allergic reactions.

14. The needle free injector of claim 4, configured to deliver in a way selected from subcutaneously, intra-Dermally, intra-Muscularly.

\* \* \* \* \*